United States Patent [19]

Hare et al.

[11] Patent Number: 4,846,165

[45] Date of Patent: Jul. 11, 1989

[54] WOUND DRESSING MEMBRANE

[75] Inventors: Pamela H. Hare, Georgetown; Steven R. Jefferies, Milford, both of Del.

[73] Assignee: Dentsply Research & Development Corp., Milford, Del.

[21] Appl. No.: 944,476

[22] Filed: Dec. 19, 1986

Related U.S. Application Data

[63] Continuation-in-part of Ser. No. 935,455, Nov. 26, 1986, Pat. No. 4,813,875, which is a continuation-in-part of Ser. No. 636,136, Jul. 31, 1984, abandoned.

[51] Int. Cl.$^4$ .................. A61L 15/00; A61C 15/01; A61M 31/00
[52] U.S. Cl. ...................... 128/156; 604/54; 604/890.1; 433/229; 424/435; 522/908
[58] Field of Search ............. 433/229, 215, 229, 80, 433/201.1, 9; 604/890, 48, 49, 54, 57, 77, 304, 310, 311; 128/82.1, 155, 156, 787; 424/425, 434, 435, 443, 486, 487; 514/964, 965; 523/111, 109, 118, 116; 525/920, 937; 522/908

[56] References Cited

U.S. PATENT DOCUMENTS

| | | | |
|---|---|---|---|
| 3,219,527 | 11/1965 | Gurney | 424/435 |
| 4,010,545 | 3/1977 | Kilian et al. | 433/9 |
| 4,097,439 | 6/1978 | Darling | 260/31.2 |
| 4,133,723 | 1/1979 | Howard . | |
| 4,173,682 | 11/1979 | Noomen et al. . | |
| 4,174,307 | 11/1979 | Rowe . | |
| 4,188,455 | 2/1980 | Howard | 525/920 |
| 4,200,762 | 4/1980 | Schmidle | 525/920 |
| 4,216,267 | 8/1980 | Lorenz et al. . | |
| 4,233,425 | 11/1980 | Tefertiller et al. | 525/455 |
| 4,250,248 | 2/1981 | Faust . | |
| 4,254,230 | 3/1981 | Howard | 525/920 |
| 4,258,164 | 3/1981 | Berlin et al. | 526/301 |
| 4,260,703 | 4/1981 | Hodakowski et al. | 525/920 |
| 4,374,969 | 2/1983 | Frisch, Jr. | 528/69 |
| 4,383,091 | 5/1983 | Burton | 525/528 |
| 4,411,754 | 10/1983 | Kaetsu et al. | 128/156 |
| 4,425,472 | 1/1984 | Howard et al. . | |
| 4,451,627 | 5/1984 | Frisch, Jr. et al. | 526/192 |
| 4,452,964 | 6/1984 | Saracsan . | |
| 4,453,063 | 9/1984 | Cohen | 433/201.1 |
| 4,457,818 | 7/1984 | Denyer et al. | 525/920 |
| 4,483,759 | 11/1984 | Szycher et al. . | |
| 4,533,326 | 8/1985 | Anthony | 433/229 |
| 4,614,787 | 9/1986 | Szycher et al. | 604/304 |
| 4,672,080 | 6/1987 | Masaoka et al. | 525/920 |
| 4,677,139 | 6/1987 | Feinaanna et al. | 128/156 |
| 4,764,377 | 8/1988 | Goodson | 424/435 |

Primary Examiner—C. Fred Rosenbaum
Assistant Examiner—Sharon Rose
Attorney, Agent, or Firm—David E. Wheeler; Edward J. Hanson, Jr.

[57] ABSTRACT

Disclosed is a method for producing an intra-oral dental bandage membrane and/or therapeutic membrane containing therapeutic agent. Actinic light is used to polymerize the membrane composition material to fix the composition in position locked with rigid dental structure such as teeth. The polymerizable substance is manipulated and shaped in a fluid state and then set, as shaped very rapidly in situ. Also disclosed is a new treatment membrane that in a preferred form is a non-symetrical oligomer that is a urethane polyacrylate.

18 Claims, No Drawings

WOUND DRESSING MEMBRANE

RELATED APPLICATIONS

This application is a continuation-in-part of application Ser. No. 935,455, filed Nov. 26, 1986, now U.S. Pat. No. 4,813,875, issued Mar. 21, 1989, which is in turn a continuation-in-part of Ser. No. 636,136, filed July 31, 1984, now abandoned.

BACKGROUND OF THE INVENTION

The present invention is concerned with bandages and other treatment membranes for mammals, especially for dental applications in the oral cavity or mouth to be mechanically retained in position by the teeth in humans. The treatment membrane is contemplated to have medical applications beyond dentistry.

Periodontal diseases and other dental diseases and difficulties affect a significant percentage of the population, causing defects in bony supportive structure of teeth and deterioration of the attachment of the tooth to soft tissue. It is often necessary to conduct one or more forms of surgery to correct anatomical defects which are the consequence of the disease, or to eliminate the microbiological milieu which is responsible for the progression of the disease. Thus, surgically removing soft tissue or bone may be a treatment to allow better access for plaque removal by the patient; or tooth substance and adjacent tissue may be surgically removed to eliminate the microbiological infection; or teeth and adjacent tissue may be surgically removed to prepare for dentures or as a consequence of carious destruction of the natural dentition. In many of these cases a dressing is desirably placed to protect the defect or wound site, for example, protecting soft tissue and sutures after surgery.

Present dressings are typified by combinations of metallic oxides and organic acids that are mixed together immediately prior to use, most frequently as two pastes which react in-situ to form hard, brittle, opaque compounds. Frequently one of the reactants is weakly acidic, a carboxylic acid or a phenolic compound, e.g. eugenol, or the like. The weak salts that form and are the structural basis of the compound are hydrolytically unstable. Saliva may leach these reactants as they hydrolyze. In due course the products crumble and disintegrate and the patients swallow or expectorate the fragments. The leached structural products frequently are unpleasant tasting and are otherwise undesirable.

Another class of compounds relies on the reaction of calcium sulfate hemihydrate, dispersed in a water permeable mixture of precured polymer and solvent. Sometimes the compounds contain inert filler, and water from the saliva is used to react with the calcium sulfate hemihydrate to form gypsum. This reaction occurs relatively slowly, and frequently the products are disintegrated before they can carry out their requisite protective function.

Yet another class of prior known materials is the combination of a polymer, polyethyl methacrylate and a solvent mixture frequently comprising a plasticizer such as esters of phthalic acid and ethanol. The plasticized pseudoelastomer which forms as the polymer solvates has poor elastic properties and develops slowly. The progression to adequately high viscosity requires from 10 to 30 minutes. No polymerization occurs. As the alcohol and plasticizer are eluted in time in the mouth the mixture becomes increasingly hard.

Each of these materials depend on the reaction, (for purposes of this discussion the solvation of a polymer by a solvent is classified as a reaction), between two or more previously separated components which are combined together and allowed to harden in-situ. In the first case, metal ions and organic carboxylic acids or phenolic compounds react, in the second case calcium sulfate hemihydrate and water (saliva); and in the third case, polymer powder and solvent.

It is an object of the present invention to provide methods and materials that overcome the deficiencies of the known dental wound dressings: to provide new methods and materials that provide treatment membranes that are long lasting and resist destruction between dental appointments, and are easy and quick to apply with good retentive properties and are useful for wound dressings, stents and other treatment purposes.

Another object of the present invention is to obviate the need for two separate components, and to obviate the time delay and inconvenience which are a consequence of mixing and having them react at their pretimed schedule within the mouth.

Another object is to provide a treatment membrane material that is fluid and has adequate manipulation time after placement to allow adapting the treatment membrane material to the site to be treated and then provides a means for quickly setting the fluid to convert the fluid to a solid.

Yet another object is to permit prepackaging of a bandage, especially of the wound or periodontal dressing type, within a syringe from which the wound dressing can be extruded inter-dentinally for mechanical retention, and directly upon a wound surface as required.

Another object is the provision of a bandage which may be mechanically retained by etched patterns in the enamel of teeth.

A further object of the invention is to provide a treatment membrane that is pigmented so as to be aesthetically less noticeable when in place in the oral cavity (mouth) of a patient.

Another object is to provide a treatment membrane that is translucent or clear, allowing inspection of the wound site without removal of the membrane.

Yet a further object is to provide a treatment membrane in a preferred form that is resilient and non hardening and thereby gentler to soft tissue with which it is in contact, an aid to patient comfort and aids in the longevity of the treatment membrane in the hostile environment of the oral cavity.

A further object is to provide a treatment membrane that is moisture resistant and non-fouling.

A still further object of the invention is to provide a treatment membrane that yields a continuing dose of therapeutic material over a period of time.

SUMMARY OF THE INVENTION

The present invention in a preferred embodiment of one of its aspects is a method for producing an intra-oral bandage using actinic light to polymerize a composition to fix the composition in position between the teeth, around a tooth, or affixed to an acid etched portion of a tooth, or in similar association with other rigid dental structure. In one preferred embodiment of the invention in one of its aspects, a polymerizable substance is provided that can be manipulated and shaped in a fluid state for a substantially prolonged period of time and then set as shaped very rapidly in situ when desired, forming a bandage. The setting is preferably carried out through the initiation of a chemical reaction by actinic light, especially light within the visible light range.

By another aspect of the invention, a treatment membrane is provided that is a polymeric membrane substantially free of leachable undesirable toxic substance and amenable to inclusion of therapeutic leachable substances.

By yet another aspect of the present invention, the polymeric membrane includes a therapeutic substance preferably distributed substantially uniformly throughout its mass, from the surface to its innermost dimension.

By a further aspect in certain preferred embodiments, a new treatment membrane is provided having medical applications beyond dentistry.

DEFINITIONS

A "treatment membrane", which is the broader concept of the present invention, includes both the method of providing a bandage and the method of holding therapeutic agent in position. The treatment membrane can be exclusively a bandage, exclusively a therapeutic agent treatment yielder or both combined. "Bandage" as used in the present patent application means a flexible strip, band or piece used to cover, strengthen, or compress: included are strips or patches used especially to dress and/or bind up wounds in the oral cavity. "Dental bandage" means a bandage used in the oral cavity or in association with dental. "Wound dressing" as used in this patent application means a material applied to cover a lesion.

By "rigid dental structure" it is meant to include natural teeth as well as other structure, such as bridge work, crowns, veneers and solid implants attached to bone structure and the like. "Fluid" as used in this application shall be understood to include not only very fluid materials that pour and run readily, but also viscous and gelatinous materials and materials that have paste and putty consistencies, all of which are fluid or are readily flowable when pressure is applied causing them to assume permanent new shapes before polymerization as compared to solid elastomeric materials which flow when subjected to force but return to substantially their original shape when the pressure is released. "Set", means to change from a fluid state to a solid state which may be in the form of a rigid solid or an elastomeric solid. By "therapeutic agent" it is meant any agent applied or provided as a treatment of disease or disorders and these include desensitizing and anesthetic agents which aid in relieving discomfort, antiseptic agents which are preventative agents, as well as antibiotics and the like. By tissue it is meant both soft tissue, such as mucosa, and hard tissue such as bone and teeth.

The treatment membrane of the present invention is to be distinguished from sealants used to seal pits and fissures and filling materials used to fill cavity perparations. However, the methods of the treatment membranes of the present invention are intended to include the positioning of the claimed materials for treating areas of the teeth adjacent to the gum or soft tissue with desensitizing agents and the like. Also the treatment of the oral cavity to treat for microorganisms that cause dental caries is included within the perview of the present invention, within the scope of a treatment membrane. By "dentist" it is meant to include those surgeons who work in the area of the mouth and surrounding structure, orthodontist, periodontist, dental auxiliaries such as hygienist and the like.

DESCRIPTION OF THE PREFERRED EMBODIMENT

The present invention in one preferred embodiment is a method of producing a treatment membrane in situ in the oral cavity of a mammal. To produce the treatment membrane a fluid polymerizable composition comprised of polymerizable organic compound and photoinitiator is applied as a fluid composition in sufficient juxtaposition to rigid dental structure to provide a mechanical locking with the rigid dental structure upon the polymerization or setting of the fluid polymerizable composition. The setting of the composition mechanically locks the set composition to the rigid dental supporting structure producing the treatment membrane in situ in the oral cavity, that is to say inter-orally. The enamel of teeth may be etched with phosphoric acid solution to retain the bandage wholly or in part.

The polymerizable organic compound is preferably an oligomer, more preferably a urethane acrylate oligomer with a reaction functionality of at least two. The photoinitiator is preferably an actinic light initiator activated in the visible light range. The setting of the polymerizable compound is in response to engagement of a surface of the fluid polymerizable composition by actinic light. The fluid polymerizable composition is preferably a one-component composition that is shelf stable when stored actinic light free. The composition is preferably applied from a syringe and caused to flow to completely surround at least one tooth to provide mechanical locking, preferably in direct contact with the tooth. The setting of the composition would then be with the fluid polymerizable composition completely surrounding the tooth and forming in one preferred embodiment a bandage, in another preferred embodiment a therapeutic membrane and in yet another preferred embodiment a bandage that is a therapeutic membrane.

In one preferred embodiment therefore, a method is provided for producing an inter-oral drug delivery device in situ in a mammal. In this method the fluid polymerizable composition preferably includes the therapeutic substance homogeneously mixed throughout and the setting or curing of the polymerizable composition does not preclude the therapeutic substance from diffusing from the treatment membrane, but rather provides a treatment membrane structure from which the therapeutic substance is leachable or metered into the oral cavity for a period, preferably a period of at least one week.

DETAILS OF FLUID POLYMERIZABLE COMPOSITIONS OF THE PRESENT INVENTION

Organic prepolymers that have a reaction functionality of at least two are suitable for constituting the polymerizable organic compound used in the present invention. Preferred are the urethane polyacrylate prepolymers. Examples of urethane polyacrylate prepolymers that are preferred include: The adduct of 1 mole of polytetramethylene glycol or polyethylene glycol and their polymers with 2 moles of hexamethylene diisocyanate or another difunctional isocyanate to which is added 2 moles of hydroxy ethyl or hydroxypropyl methacrylate; the adduct of 1 mole of polytetramethylene glycol and 2 moles of an isocyanato ethylmethacrylate; and the adduct of 1 mole of trimethyl hexamethylene diisocyanate and 2 moles of hydroxypropylmethacrylate.

One, more preferred urethane polyacrylate prepolymer, is one having the following general formula:

$R_1\text{---}[A]\text{---}R_2$ $R_1$ is

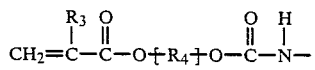

$R_2$ is

$R_1$ and $R_2$ each independently preferably have from 5 to 100 C, more preferably 5 to 15 C and most preferably 6 to 11 C.

$R_3$ is H, alkyl, sub alkyl, aryl, sub aryl, F, CN. (The term sub as used in this application means substituted, which means that at least one non C or H atom would be present or a radical such as a benzene ring would be present. By arcylic it is meant any pendent acrylic radical, by diacrylic it is meant a radical or a compound with two pendent acrylic radicals.)

$R_3$ may be the same or different in each position.

$R_3$ is preferably methyl.

$R_4$ is a divalent hydrocarbon radical or divalent sub hydrocarbon radical and may be straight or branched chain or cyclic or a combination thereof. By cyclic it is meant to include aromatic and heterocyclic compounds.

$R_4$ preferably has from 2 to 100 C, more preferably $R_4$ is an aliphatic radical having from 2 to 100 C, more preferably 2 to 10 C and most preferably 2 to 6 C.

A is any polyurethane oligomer. (By poly as used in this application it is meant two or more. By oligomer it is meant a molecular weight of at least 250, more preferably 400 and most preferably 600 or more. The term backbone as used in this application means the structure of the oligomer between the two urethane groups closest to the terminal ends of the molecule). $R_4$ may be the same or different in each position.

The presently more preferred composition, which is an important aspect of the present invention, is A is $\text{---}[R_5]\text{---}X\text{---}[R_6]\text{---}$ $R_5$ and $R_6$ are each independently divalent hydrocarbon radicals or divalent sub hydrocarbon radicals and may be straight or branched chain or cyclic or a combination thereof and may also be siloxane or sub siloxane radicals.

$R_5$ and $R_6$ preferably have from 2 to 100 C, more preferably $R_5$ and $R_6$ are aliphatic radicals having from 2 to 100 C, more preferably 2 to 10 C.

$R_5$ and $R_6$ may be the same or different.

X is a polyurethane and $R_5\text{---}X$ and $R_6\text{---}X$ are joined by a urethane linkage.

X may broadly contain any hydrocarbon or sub hydrocarbon radical and may be straight or branched chain or cyclic or a combination thereof and may also be one or more of the following radicals: siloxane, sub siloxane, sulfone, etc., but is preferably a polyether or a polyester or mixture thereof, most preferably X is a polyether and the polyether radical is straight chain, of course as a polyurethane.

It should be clear from the above general formula that it is not considered critical to the present preferred prepolymer in its broader aspects what the radical —A] may be so long as it is a hydrocarbon or sub hydrocarbon and a polyurethane. Beyond this the person skilled in the art would tailor the radical to achieve such characteristics as they may choose. However, the asymmetry of $R_1$ and $R_2$ are a central feature of the present invention and are believed to constitute a significant advance in the art of urethane polyacrylates. The particularly preferred —A] radical, especially with both $R_5$ and $R_6$ joined to X by a urethane linkage with X being of substantial molecular weight and both $R_5$ and $R_6$ of low molecular weight, is of special preferred merit, especially in the more preferred embodiments of the present invention.

$R_1$ is a radical preferably formed by reacting a hydroxy acrylate with an isocyanate group on a prepolymer polyurethane oligomer and is drawn to include the urethane group contributed by the isocyanate.

$R_2$ is a radical contributed entirely by an isocyanato acrylate when the isocyanato acrylate is reacted with a hydroxy group on a prepolymer polyurethane oligomer.

In $\text{---}[R_5]\text{---}X\text{---}[R_6]\text{---}$, $R_5$ would be the terminal radical in the prepolymer polyurethane oligomer when the terminal urethane group has been drawn as part of $R_1$. For clarity of explanation, in Example 1 this would be the trimethyl hexamethylene radical from trimethyl hexamethylene diisocyanate and would include the other urethane group contributed by the diisocyanate. $R_6$ would be the oxyalkylene residue of the 1,4 Butane diol.

The more preferred compound has the formula:

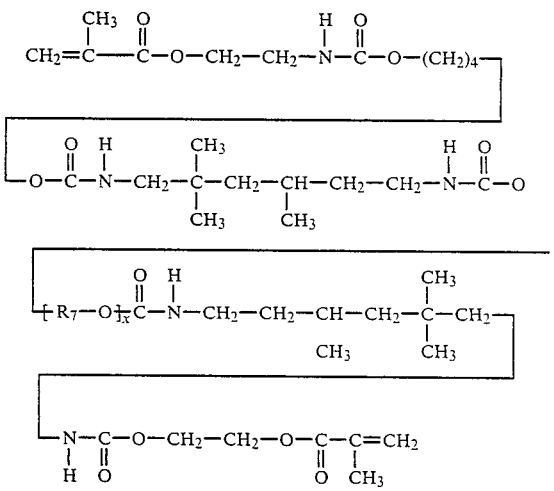

wherein $R_7$ is Alkylene, sub alkylene.

x is 10 to 100.

The method of producing the preferred non symmetrical urethane polyacrylate prepolymers is revealed in detail in Example 1 and with greater explanation in U.S. Ser. No. 935,455 the contents of which are incorporated herein by reference.

Mixtures of the above given exemplary prepolymers and other similar oligomers may be used as the sole polymerizable ingredient; or the fluid polymerizable composition may include diluent comonomers such as—other lower viscosity diluent monomers and oligomers, for example polyethylene glycol dimethacrylate, butylene glycol dimethacrylate and the like. All diluent monomers are characterized as having low volatility and toxicity.

Additional exemplary prepolymers for use in the present invention include: polysiloxanedimethacrylates, polyorganosilylenes—for example—polydimethyl-silylene-co-phenylmethylsilylene, polycarbonate urethane dimethacrylates, Ethoxylated bisphenol A dimethacrylate, 2,2-Bis[4-(3-methacryloxy-2-hydroxypropoxy)-phenyl]propane (BISGMA), and 2,2-Bis[4-(2-methacryloxy-2-methylethoxy)phenyl]propane (BISIPMA).

The dental treatment composition material of the present invention in its preset, fluid form is preferably substantially stable against assuming a permanent remembered form when stored actinic light free. The composition is preferably stable when stored as a single one-component material for a long period of time actinic light free, preferably being stable for at least two months, more preferably six months, and most preferably for one year or more. By one-component, it is meant that the treatment membrane material can be stored in the exact form that it will be used in by the dentist, so that the dentist preferably does not need to do anything other than mold the composition to the surface (surfaces) that are to be protected, treated or retain the treatment membrane and then cure the treatment membrane material by exposing it to actinic light to form the treatment membrane.

The preferred embodiment providing a shelf-stable storable treatment membrane material is one having a photoinitiating system. The photoinitiating system may be one of many known in the art to promote polymerization of unsaturated acrylic groups when activated by actinic light of the appropriate wavelengths, strength and length of exposure time. Such systems include, but are not limited to camphoroquinone and other alphabeta diketones, alone or with reducing agents, such as secondary and tertiary amines, compounds known to be accelerators for photopolymerization of acrylates upon irradiation by visible light. Materials such as benzoin and benzoin methyl ether which are known to be photopolymerization initiators utilizing light in the near UV portion of the electromagnetic spectrum are operable to cure the presently preferred polymers, but UV light is considered generally undesirable in most instances because of possible interactions with living tissue.

The actinic light activated photopolymerizable composition is for health and safety reasons preferably one that can be expeditiously cured using light filtered to limit the wave lengths to the visible light range of approximately 360-600 nanometers. More preferably the curing is carried out with the greater portion of the light being within the 400-500 nanometer range.

The amount of photopolymerization initiator or sensitizer and the types are selected with due consideration to the intensity of the intended light source and the activating wavelength(s) and their capacity to initiate polymerization. Photoinitiators, for example, camphoroquinone, are preferably used in concentrations between 0.001 and 10% by weight of the polymerizable resin present, more preferably between 0.01 and 5%. Accelerators for the photoinitiation for example, tertiary amines, including, for example, methyldiethanolamine, diethanolamine, triethanolamine, 4-ethyldimethylaminobenzoate, or 4-dimethylaminobenzonitrile may be used. These are preferably used in amounts of between 0.001 and 10% by weight of the polymerizable resin present, more preferably between 0.01 and 5%.

The dental treatment membrane is preferably a viscous liquid, or it can be modified with fillers to result in more viscous pastes or even putties. It is important in some cases that these materials be moldable using the gloved finger of a dentist or an instrument so that the material ma be adapted between the teeth, or pressed against a tooth to obtain retention by the acid micro etched patterns upon enamel. The addition of solid fillers is a means to facilitate this, but they must be chosen to have suitable optical characteristics so as not to interfere with the transmission of actinic light through the material to initiate polymerizatiion. The filler particles should have size and surface area appropriate to effect the desired viscosity change.

Generally the fillers are chosen primarily for viscosity modification but they may also be used to influence the bonding properties of the treatment membrane as well. Reinforcing fillers may also be used to improve the strength of the treatment membrane. Typically reinforcing fillers will have particle sizes of less than 1 micron and appropriate surface treatments to enhance bonding with the polymerizing oligomeric polymer. Preferred reinforcing fillers have a surface area of at least 50 square meters per gram and are exemplified by pyrogenically-produced silicon dioxide, silicic acid hydrogels dehydrated so as to maintain their structure, silicon dioxide, and precipitated silicon dioxide, with preferred particle sizes between 0.001 and 1.0 microns. The non reinforcing fillers may be larger in size, for example up to 250 microns, and they also may not be surface treated. Typical fillers include calcium carbonate, fused quartz powder, powdered calcium silicaluminate, titanium dioxide, zirconium silicate, aluminum silicate, crystobalite, feldspar, etc. Preferred fillers include silicon dioxide such as fused quartz. The fillers may be ground or formed by a variety of means including polymerization as microspheres to provide particulate powdered filler of preferred sizes between 1 and 250 microns, depending on the application. Particles of individual average sizes of 1 and 100 microns are especially preferred.

All of these fillers; but especially the reinforcing fillers, can have organosilyl groups on their surface if they have been pretreated, for example, with dimethyl-halogen silanes, for example by reaction of aqueous silica sol with organo halogensilanes, or have been rendered hydrophobic in some other way. Mixtures of different fillers can be used. Non-reinforcing fillers may in some instances be used at concentrations of up to about 80%, more preferably limited to less than 60% by weight based on the total weight of the fluid treatment membrane composition material. Reinforcing fillers may be appropriately used in the compound in an amount of from 1% to 80% by weight, based on the total weight of the fluid treatment membrane composition material, more preferably 10–40% and most preferably 15 to 30%. Preferred overall filler contents are from 5 to 95% more preferably 20 to 90% and most preferably for some applications 40 to 85% by weight based on the total composition weight. An important consideration is that the amount and the type of filler is so selected that actinic radiation may pass through the mass to cause polymerization throughout, but the filler need not match the refractive index of the resins exactly.

Dispersants and surface active agents may be included to aid in the dispersion and combining of the fillers and pigments and better bonding with the polymerizable matrix oligomers. Alkyl benzensulfonyl titanates are preferred dispersing agents for fillers in the free radical initiated polymerizable resin. A preferred alkyl benzensulfonyl titanate is neoalkoxy, tridodecylbenzenesulfonyl titanate (Titanium IV neoalkoxy, tris(-dodecylbenzene)sulfonato). The titanate is preferably present in an amount of 0.001 to 2% by weight of the total composition, more preferably 0.005 to 1% and most preferably 0.01 to 0.5%.

Another important embodiment of the present invention provides treatment membranes which serve as a repository and long term dispenser of a wide range of therapeutic agents useful in treating mammals. These therapeutic agents may be incorporated into the treatment membrane of the present invention by mixing or encapsulation.

Examples of therapeutic agents include those for treating infection by such organisms as Streptococcus mutans (which is causally implicated in dental caries), or A. actinomycetemcomitans and B. gingivalis (which are causally linked with periodontal disease), or the like. Exemplary of these therapeutic agents are the following examples arranged by structure and clinical use:

1. Antiseptics and Germicides
   a. ethanol and isopropanol
   b. iodine preparations
      (1) iodine, U.S.P.
      (2) Providine-Iodine
      (3) iodoform
   (4) thymol iodine
   c. thimerosal (Merthiolate)
   d. oxidizing agents
      (1) urea peroxide
      (2) chlorine dioxide
      (3) benzoyl peroxide
   e. Phenolic Compounds
      (1) eugenol, U.S.P.
      (2) Guaiacol (2-Methoxyphenol)
   f. Quaternary Ammonium Compounds
      (1) Benzalkonium Chloride. U.S.P.
      (2) Benzethonium Chloride (Phemerol Chloride)
2. Non-antibiotic Antimicrobials
   a. Chlorhexidine
   b. Silver Nitrate (1%)
   c. silver sulfadiazine (1%)
3. Antibiotics
   a. Penicillins
   b. Tetracyclines
   c. Erythromycins
   d. Cephalosporins
   e. NBH (1% neomycin, 1% bacitracin. 0.5% hydrocortisone)
   f. metnanidasole
4. Antifungal agents
   a. triacetin
   b. ciclopirox olamine
   c. clotrimazole
   d. griseofulvin
   e. miconazole nitrate (2%)
   f. Castellani Paint (basic Fuchsin, Phenol, Resorcinol, acetone, alcohol.
   g. amphotericin B
   h. Nystatin
5. Steroidal Antiinflammatory agents
   a. Triamcinolone acetonide (0.1%)
6. Non-steroidal antiinflammatory agents
   a. salicylates
   b. indomethacin
   c. ibuprofen
   d. fluoribuprofen
   e. 2-[3-(1,1-dimethyl)-5-methoxyphenyl]oxazolo[4.5b]pyridine
7. Antiviral agents
   a. triamcinolone
8. Non-fluoride tooth desensitizing agents
   a. strontium chloride 10%
   b. sodium citrate 1.5%
   c. Potassium Nitrate 5%
9. Wound healing agents & anti-collagenase (protease) agents
   a. fibronectin (plasma)
   b. tripeptides
   c. short chain peptides up to 20 amino acids in length which exhibit wound healing or anticollagenase (antiprotease) or antielastase activity.

Therapeutic agents can be included, such as those that treat caries by providing locally high concentrations of remineralizing chemicals, as exemplified by those yielding calcium ion, fluoride ion, and phosphate ion. Such therapeutic agents are exemplified by sodium fluorophosphate, tricalcium phosphate, sodium fluoride, calcium fluoride, etc.; or antiseptic compounds, for example, chlorhexidine.

Therapeutic agents may be included for sedating the tooth by applications of locally high concentrations of topical anesthetic or metal cations, hydroxyl ions, and the like, which can obturate the dentinal tubuli to avoid sensitivity. Such therapeutic agents would be exemplified by benzocaine, strontium chloride, calcium hydroxide, and the like. The therapeutic agents useful in the present invention may be solid or liquid, inorganic or organic.

It will be understood that the aforementioned exemplary therapeutic materials, or their equivalents, are preferably uniformily dispersed throughout a treatment membrane compositiion to provide for diffusion at a rate determined solely by their dispersion through the polymerized composition. Alternatively the therapeutics may first be combined with other ingredients separately to provide for their microencapsulation in a first solid uniformly or, they may be dispersed through a first slid and comminuted to form particles of, preferably, less than 250 microns size, which then are dispersed through the fluid polymerizable composition to further regulate their diffusion. For example, the agents may first be microencapsulated within gelatin or dispersed within microparticles of, e.g. polyvinyl alcohol. The preferred prepolymerized microparticles are preferably composed of polymer, chosen from the group of water soluble and water dispersible polymers and mixtures thereof. The microparticles act as reservoirs for the therapeutic agent. The microparticles preferably should be less than 250 microns in size.

It will be understood that these carrying or accompanying substances containing or accompanying the therapeutic agent would in preferred embodiments be uniformly dispersed throughout the fluid treatment membrane composition material from the outer surface throughout the inner thicknesses of the bandage. After curing, in preferred embodiments, these dispersed domains of relatively high therapeutic concentration may aid in the metering and more uniform leaching of the therapeutic agent into the treatment area over a period of time. The carrying or accompanying substance may also aid with the general dispersion and retention of the therapeutic agents within the polymerizable composition.

Other formulation auxiliaries may also be included in the treatment membrane material. Organic polymers, for example polyvinyl pyrrolidone or methacrylate polymer powder, polyvinyl alcohol and the like, may be used as fillers, extenders and plasticizers. Stabilization of these compositions against premature polymerization may be achieved by the addition of hydroquinone, catechol, and other similar well-known polymerization inhibitors for the polymerization of (meth) acrylate compounds. Other optional ingredients include pigments and flavoring substances. Still other plasticizers may be included, for example, siloxanes, phthalates, glycerides, and other materials known to the art. Such plasticizers are generally added to alter the hydrophobicity, the softness or hardness of the composition, its viscosity or tackiness, etc.

A preferred treatment membrane has an elongation in tension of at least 1%, more preferably 3% and most preferably 10%; a strain in tensil of at least 5% more preferably 10% and most preferably 20%; and a modulus of elasticity of at least 100 psi, more preferably 200 psi and most preferably 400 psi.

The preferred treatment membranes of the present invention when used for periodontal wound dressings have the desirable property of resisting ingress of healing tissue into the membrane itself and thereby lends itself to easy removal from soft tissue of the oral cavity. Such an especially preferred treatment membrane is comprised of the non-symmetrical urethane polyacrylate polymer described in this invention and shown, for example, in Example 1. Except where teeth are deliberately acid etched for retention of the treatment membrane the preferred treatment membrane material provides for ready release, non-adhering characteristics relative to rigid structures in the oral cavity, both natural dentition and artificial, after curing. This offers the advantage of easy removal to avoid damaging protected structures unintentionally, especially soft tissue structure in the process of repair. The preferred treatment membrane material also is substantially non-toxic in use and non-allergenic.

The preferred treatment membrane material can be readily cured in direct contact with living mammalian tissue.

DETAILED DESCRIPTION OF APPLYING THE METHOD OF THE PRESENT INVENTION

The treatment membrane formulation or material is preferably prepackaged in a syringe. The treatment membrane material is then applied directly from the syringe to the surfaces to be provided with the treatment membrane. The fluid material is then shaped and molded with an instrument or the finger to position it in relation to the structure to be provided with the treatment membrane and also with relation to any structure that will hold the bandage in position. Preferably a disposable glove is used and it may be lubricated with a thin film of a material such as vaseline, lanolin or cold cream or the like. Preferably the rigid dental structure that will hold the treatment membrane in position is cleaned and dried before application of the treatment membrane material to it. Dental enamel may be microetched, for example with 30% phosphoric acid by procedures well known to the art, for better intraoral retention. The treatment membrane material is cured by exposing it to actinic light. The material can be checked for coverage and position and additional material may be added and cured as desired. In the case of preferred treatment membrane materials, the additional material bonds to the cured original treatment membrane and is not easily dislodged therefrom.

Not only can the treatment membrane serve as a bandage covering an area to keep food, fluids, and other debris from contaminating the area, but in instances where a wound is not severe or where conservative surgery has been done the bandage may act as a stint to maintain closure eliminating the need for sutures. An example of when this might be particularly applicable would be in the case of conservative periodontal surgery, i.e., flap currettage, gingival currettage without reflection of a gingival flap, or a modified Widman Flap procedure where the mucoperiosteal flap has not been fully reflected to expose the alveolar crest. In such selected instances, proper positioning of the fluid bandage may act as a wound closure device, reducing or totally eliminating the need for non-absorbable or absorbable suture placement. The fluid bandage, when polymerized, could act as a wound closure stent, as well as protective bandage.

On occasion it may also be desirable to build up the treatment membrane in layers by placing individual coatings of fluid bandage material in position and curing them. Preferably the layers would be in thicknesses of about 0.5 to 3 mm and might be applied three or four coatings or layers deep, curing each in turn. This procedure can in some instances provide superior wedging and positioning of the treatment membrane in the embrasures between and around the teeth or locking with other rigid dental structures. Additions may be added to the cured bandage at any time. For example, if a portion of the bandage does become dislodged for some reason, the cured fluid bandage material does not have to be totally removed and replaced, as is currently commonly required. Increments of the fluid bandage material may be applied to the existing intra-oral bandage segment and cured, thus giving an augmented bandage which is then fully functional and cohesive as a single unit.

In its preferred form, the method includes aspects of the materials that can perform the needed actions for preferred performance of the preferred methods of the present invention. The preferred method does not require pre-mixing of the composition before it is used. The compositions are preferably flowable, deformable and substantially free of any shape memory prior to activation by actinic light so that the composition can be formed to the desired shapes of treatment membranes against both the rigid and soft tissue surfaces of the oral cavity.

The one-component composition of the present invention can be packaged in various ways including the preferred preloaded syringes, from which the dentist can express the material directly onto the soft or hard tissues of the oral cavity. The composition can also be preloaded into a dental tray which can be placed by the dentist directly into the mouth of the patient, or it can be preloaded into a collapsible tube from which the dentist can squeeze the material onto a dental tray shaped to force the material against the teeth. The tray can be of a material that passes actinic light. An important point is that the container package overwrap be metal, or otherwise be opaque to actinic light, or be packaged in such a manner as to protect the composition of the invention from actinic light prior to use by the dentist. Of course, the tray would usually be configured to adapt the material around a given area, not to provide full coverage of teeth as when taking a dental impression.

The actinic light is preferably visible light from a source such as the PRISMETICS ® lite and PRISMA-LITE ® polymerization units of the L. D. Caulk Company, which produces visible light with a band of wavelengths between 400 and 500 nanometers and an energy output of approximately 400 milliwatts per square centimeter from the tip of the unit's light guide. The polymerization time can vary depending on the intensity and wavelength of the light used and the quantity of material to be polymerized, but is preferably two minutes more preferably one minute, given the above conditions.

The composition of the present invention is stable against premature polymerization. The composition is preferably non-toxic in use in the oral cavity; stable in storage for at least six months as a one-component composition when actinic light free; and assumes a permanent memory when exposed to light filtered to limited wavelengths within the visible light range for one minute to a depth of at least three millimeters.

The invention is further illustrated by the following examples:

EXAMPLE 1

Resin 1 Preparation

A preferred isocyanatoethyl methacrylate urethane methacrylate oligomer elastomer prepolymer compound was prepared according to the following formulation

| | |
|---|---|
| Polypropylene glycol (MW 4000) Voranol 2140 (Dow Chemical) | 834.6 g |
| Trimethylhexamethylene diisocyanate (Thorson Chemicals) | 87.7 g |
| Stannous octoate | 0.50 g |
| Hydroxyethyl methacrylate (Rohm & Haus) | 27.1 g |
| 1,4 Butanediol (BASF) | 18.7 g |
| Isocyanatoethyl methacrylate | 30.8 g |

The procedure was as follows:

In theory, one mole of polypropylene glycol (2 equivalents of hydroxy) are reacted with two moles of trimethylhexamethylene diisocyanate (4 equivalents of isocyanate) employing the stannous octoate as catalyst.

The polypropylene glycol was charged into a 2 liter reacter. Stirring and dry air flow through the reactor was begun. The stannous octoate was charged to the reactor and allowed to stir in. Then the trimethylhexamethylene diisocyanate was added to the glycol catalyst mixture dropwise using a separatory funnel. The addition was done at room temperature and was controlled to keep the temperature below 50° C. Addition was complete after 30 minutes. The contents were allowed to stir for 30 minutes more. Samples were taken and titration was done to determine isocyanate content. Isocyanate was found to be 1.9% which indicated complete reaction of the polypropylene glycol and trimethyhexamethylene diisocyanate. Then the 27.1 grams of HEMA were added all at once to the reactor contents which were at a temperature of about 40° C. The contents were allowed to stir for 45 minutes. Then titration samples were taken and the isocyanate content determined to be 0.95%. This indicated complete reaction of the HEMA with the isocyanate terminated prepolymer leaving 1 equivalent of isocyanate sites for reaction with 1,4 butane diol. At this point 18.7 grams of 1,4 butane diol were added to reactor contents all at once and allowed to stir in for 2 hours. The temperature of the reactor continued between 40° and 50° C. for this procedure. At the end of 2 hours the isocyanatoethyl methacrylate was added dropwise to the reactor using a separatory funnel. This addition took approximately 30 minutes. Stirring was continuous until the next morning to be sure all the free isocyanate was reacted. Then the pot contents were unloaded.

Bandage Preparation

A visible light curable bandage of the following formulation was compounded by a double planetary mixer at reduced pressure. The ingredients were added in the order listed in the abscence of visible light.

| | |
|---|---|
| Resin of EXAMPLE 1 | 373.5 g |
| Camphorquinone | 0.76 g |
| 4-Dimethylaminobenzonitrile | 3.49 g |
| Butylated Hydroxy Toluene | 0.163 g |
| Titanium IV neoalkoxy, tris (dodecylbenzene) sulfanato (Ken React LICA 09 from Kenrich Petrochemicals, Inc.) | 0.30 g |
| Silanated/ground Quartz (mean particle size of 10–15 microns) | 464.8 g |
| fumed silica (Aerosil R-972 from Degussa) | 155.0 g |
| Rocket red fluorescent pigment (Dayglo) | 0.214 g |

The composition was irradiated for 10 seconds using the Prismetics ® light earlier described. A sample of material 20 mm thick was covered with a sheet of clear Mylar about 1 mil thick. The sheet was in direct contact with the sample. The light was directly engaged against the sheet of Mylar. The material cured to a rubbery solid to a depth of 13 mm. The uncured composition was removed by wiping.

Water sorption and solubility measurements were taken on the cured material with the results given below.

| | |
|---|---|
| *1 Week Water Sorption (mg/cm$^2$) | 0.61 |
| **1 Week Water Solubility (%) | 0.20 |

*Performed as in American Dental Association (ADA) Spec. #27.
**Performed as in ADA Spec. #8 except specimens were left in distilled water for one week instead of 24 hours.

The composition is non-tacky in use and bonded to acid etched tooth enamel by molding the pasty material against the tooth with a gloved finger prior to polymerizing to set using a Prismetics ® light.

EXAMPLE 2

Resin 2 Preparation

A urethane dimethacrylate was prepared according to the following formulation:

| | |
|---|---|
| Hydroxy propyl methacrylate (HPMA) | 59.18% |
| Trimethylhexamethylene diisocyanate (TMDI) | 40.75% |
| Stannous octoate | 0.05% |
| Methyl ether hydroquinone | 0.02% |

Procedure: The hydroxy propyl methacrylate stannous octoate, and methyl ether hydroquinone were weighed into a dry two liter reactor. Stirring and dry air flow through the reactor were begun. The reactor contents were heated to 50° C. and was continually stirred for 30 minutes to form a homogenous solution. The TMDI was weighed into a beaker and poured into a 250 ml. addition funnel where it was next added dropwise to the reactor. The drop rate was monitored to keep the temperature between 50°-60° C. The next morning, a sample was taken and found to be free of residual diisocyanate. Then the reactor contents were unloaded.

Resin 3 Preparation

A polyether urethane dimethacrylate was prepared according to the following formulation:

| | |
|---|---|
| Pluracol 628 (polypropylene glycol mw 4,000) | 93.61% |
| Isocyanatoethyl methacrylate (IEM) | 6.34% |
| Stannous octoate | 0.05% |

Procedure: The Pluracol 628 and stannous octoate were weighed into a dry two liter reactor. Stirring and dry air flow through the reactor were begun. The IEM was weighed into a beaker and poured into a 250 ml. addition funnel where it was added dropwise to the reactor. The addition of IEM was done keeping the temperature below 50° C. Addition took 30 minutes. After addition the contents were allowed to stir 36 hours at a temperature between 40°-50° C. Then a sample was taken, found to be free of residual isocyanate, and the reactor contents unloaded.

Bandage Preparation

A visible light bandage of the following formulation was compounded by a double planetary mixer at reduced pressure:

| *Resin mixture (Resin 2-20 parts and Resin 3-80 parts) | 241.3 g |
|---|---|
| Camphorquinone | 0.5 g |
| 4-Dimethylaminobenzonitrile | 2.2 g |
| Butylated Hydroxy toluene | 0.244 g |
| Silanated Ground Quartz (Mean particle size of 10-15 microns) | 565.1 g |
| fumed silica (Aerosil R-972) | 188.1 g |
| Neoalkoxy, tridodecylbenzene-sulfonyl titanate (Ken React LICA 09) | 2.5 g |
| Rocket Red Fluorescent Pigment (Dayglo) | 0.260 g |

*Resin 2 and Resin 3 were combined first and stirred for 30 minutes in a double planetary mill.

The composition was irradiated for 1 minute using the procedure of Example 1. The material cured to flexible solid that was substantially stiffer than the solid produced in Example 1.

EXAMPLE 3-5

A series of treatment membrane samples were prepared based upon the composition of Example 1.

Varying amounts of sodium fluoride powder sieved to less than 250 microns was added to the bandage composition of Example 1 to produce compositions 3, 4, and 5. These were made into discs having a diameter of 20 mm and a thickness of 1 mm by filling a Mylar backed stainless steel ring, inserting a small piece of nylon string, smoothing the surface, and curing for 1 minute on the top side only with a GE Photoflood lamp (EBV-NO. 2). The top surface of the disc were left uncovered. The weight of each specimen was then recorded to the nearest 0.1 mg. The discs were prepared in 3 replications and extracted individually in deionized water by suspension in 11 ml. of the water. Each day the micrograms of fluoride extracted were measured using an ion fluoride sensitive ion electrode in conjunction with a Fisher Accumet pH meter (model 825 mp). After the daily measurement was taken, the old water was discarded and fresh water was added to the specimens so that the daily extraction data was accurate. On weekends the data was collected for the three days. Original concentrations of sodium fluoride and extraction data are presented as such in the table below:

TABLE 1

| | | Micrograms Released Time (Days) | | | | | | | | | | | |
|---|---|---|---|---|---|---|---|---|---|---|---|---|---|
| Ex. | % NaF | 1 | 2 | 3 | 4 | 5-7 | 8 | 9 | 10 | 11 | 12-14 | 15 | 16 |
| 3 | 1% | 30.7 | 18.1 | 16.1 | 15.7 | 37.3 | 11.0 | 9.5 | 8.5 | 8.1 | 19.6 | 5.2 | 11. |
| 4 | 2% | 78.7 | 41.3 | 32.7 | 29.9 | 71.0 | 20.2 | 17.9 | 16.1 | 15.9 | 39.0 | 11.8 | 25. |
| 5 | 5% | 193.1 | 100.0 | 79.4 | 65.9 | 132.7 | 44.0 | 39.6 | 34.7 | 34.0 | 95.9 | 31.5 | 82. |

EXAMPLES 6-8

A series of treatment membrane samples were prepared based upon the composition of Example 2, except that sodium fluoride (−250 μm) was added. The original concentrations and extraction data (see examples 3-5 for testing procedure) are given in Table 2.

TABLE 2

| | | Micrograms Released Time (Days) | | | | | | | | | | | |
|---|---|---|---|---|---|---|---|---|---|---|---|---|---|
| Ex. | % NaF | 1 | 2 | 3 | 4 | 5-7 | 8 | 9 | 10 | 11 | 12-14 | 15 | 16 |
| 6 | 1% | 80.8 | 51.8 | 46.6 | 38.9 | 90.5 | 18.0 | 11.0 | 6.7 | 4.6 | 6.0 | 1.1 | 1. |
| 7 | 2% | 132.4 | 83.6 | 73.3 | 66.3 | 157.9 | 32.5 | 21.4 | 13.5 | 7.9 | 9.7 | 1.41 | 2. |
| 8 | 5% | 287.3 | 175.7 | 137.6 | 122.4 | 324.3 | 97.4 | 85.7 | 74.2 | 61.2 | 121.2 | 25.3 | 28. |

EXAMPLE 9

The treatment membrane formulation of Example 3 was loaded into a 3 cc syringe having a reservoir diameter of 10 mm and length of 55 mm and an outlet length of 12 mm and smallest diameter of 3 mm. The syringe was made of polypropylene.

The treatment membrane material was applied to the upper right quadrant buccal and lingual tissue surfaces of a human by the following procedure:

1. Disposable gloves were lubricated with thin film of K-Y jelly (Johnson & Johnson, Inc.)

2. The cap was removed from the syringe and the VLC perio dressing was extruded onto the juncture of the hard and soft tissue including the interproximal areas of the buccal surfaces.
3. The material was muscle molded and/or contoured with a lubricated finger or instrument to the tissues. Care is taken to avoid placement on occlusal contacting areas of the teeth.
4. The material was cured by exposing each area for 20–40 seconds with the Prismetics lite held 10 mm from the material. Curing was completed in 1 minute.
5. Occlusion and coverage of the material was checked. Additional material was added and cured for 10 seconds. The additional material was bonded and could not be dislodged from the first.
6. The material was then applied to the lingual surfaces as in step 2.
7. The material was contoured to the tissues with the lubricated gloves.
8. The material was cured as in step 4.
9. Occlusion and coverage of the material were checked. Both were satisfactory.

The product was tough, adherent, and could not be removed without some difficulty. The product was aesthetically pleasing and comfortable to wear. It was retained in place for seven days and then removed. Visual inspection with the unaided eye showed minimal adherence of bacterial plaque and minimal staining except by agents known to impart stain on existing dental restorative materials, such as coffee, tea and tobacco. However, this staining did not materially adversely effect the esthetics of the material.

EXAMPLE 10–12

A series of treatment membrane compositions were prepared by mixing the below given ingredients in a motorized mortar at ambient conditions. All of the solids were added first and mixed until uniform in appearance. The liquids were premixed and then one half of the mixed liquids were added to the mortar and mixing was continued until smooth uniform mixture was obtained. The remaining liquid was then added to the mortar and mixing was continued until the mixture was homogeneous.

| Example # | 10 | 11 |
| --- | --- | --- |
| Urethane dimethacrylate (Plex 6661 from Rohm AG) | 56.5 | 56.5 |
| triethylene glycol dimethacrylate | 28.2 | 28.2 |
| polyvinyl pyrrollidone mw 24000 | 7.4 | 0 |
| methylene blue | .01 | .01 |
| Camphorquinone | .46 | .46 |
| dimethylamine ethyl benzoate | .18 | .18 |
| silicon dioxide | 3.1 | 3.1 |
| butylated hydroxytoluene | .05 | .05 |
| sodium fluoride | 4.13 | 4.13 |
| strontium chloride hexahydrate | 0 | 3.97 |

The treatment membrane compositions were then prepared as test samples by placing ½ gram of each composition into a polyethylene container 12 mm in diameter, and 8 mm deep and filled the container to about ½ full.

The fluoride ion therapeutic agent release is expressed as micro grams of fluoride ion per 1 cm$^2$ of surface area of the specimen. The fluoride ion concentration was determined using a fluoride electrode (Phillips) with a pH meter reading in m V (Metrome). The specimen was stirred at a constant rate in 50 ml of distilled water, and readings taken at 0.5, 1, 2, 4, 6, and 24 hr. The water was then exchanged for fresh distilled water every 24 hr. and the readings were taken and the water replaced with fresh water at the next 24 hr. period.

| Ex. | ½ hr | 1 hr | 2 hr | 4 hr | 6 hr | 24 hr | 48 hr | 72 hr | 96 hr | 130 hr |
| --- | --- | --- | --- | --- | --- | --- | --- | --- | --- | --- |
| 10 | 40 | 60 | 70 | 105 | 125 | 298 | 98 | 20 | 20 | 836 |
| 11 | 32 | 52 | 67 | 90 | 103 | 163 | 49 | 13 | 18 | |
| 12* | 5 | 5 | 10 | 33 | 60 | 118 | 98 | 16 | 15 | 360 |

*Example 12 is Duraphat ® shellac, a commercial shellac composition sold as a tooth coating. The Duraphat shellac sample was tested in the same manner as described in Examples 10 and 11.

EXAMPLES 13–15

A comparison was made between current inter-oral wound dressings and the wound dressing or bandage of the present invention.

Example 13 shows the results of testing the fluid bandage composition material of Example 1. Example 14 shows the results of testing of current commercial material sold as a periodontal dressing under the brand name Coe-Pack hard and fast set supplied by Coe Laboratories, Chicago, Ill. Example 15 shows the results of testing another current commercial material sold as a periodontal dressing under the brand name Perio-Putty by Cadco.

Depth of cure was measured using the method described in example 1.

Consistency was measured as follows: A tube calibrated to deliver 0.5 ml. was packed with the materials (for example 14 the uncured material was used; for examples 15 and 16 the freshly mixed material was used) and extruded onto a sheet of polyethylene. Another sheet of polyethylene covered the material. A glass plate weighing 76 grams plus a 500 gram weight was then placed on top of the polyethylene and material for 30 seconds. Then the weight and plate was removed and the diameter of the disc was measured to the nearest millimeter. The average of three determinations is reported.

Strain in compression was measured according ADA Spec. 19. The specimen was cured for 40 seconds with the Prismetics ® lite using the 14 mm tip. The test was started one minute after irradiation was complete.

Tear strength, Elongation in tension, Strain in tension, and Modulus of elasticity in tension were all tested on an Instron (Model 1123 with hydraulic grips) and a Microcon II microprocessor.

The specimens were prepared by filling a mold prepared for the purpose. The mold was stainless steel and in the shape of the Roman Numeral I. The top and bottom cross ends were 16 mm across and the web number between was 5 mm across in the same direction. The cross ends were each 13 mm in vertical dimension and the web member was 22 mm in vertical dimension. The depth of the mold or thickness of the sample was 1.5 mm.

Specimens were prepared for example 13 by filling mold with uncured material, placing a Mylar strip (1 mil thick) on the top and bottom, pressing flat, and curing for 30 seconds under the photoflood lamp (GE EBV-No. 2). Then the specimen were demolded and placed in distilled water at 37° for 24 hours before testing. Specimens for example 14 were prepared by mixing equal lengths of base and accelerator for 30 seconds and then packing mold with material. Mylar strips were placed on top and bottom of the mold, stainless steel plates were also placed top and bottom, and the whole assembly was clamped and put into a 37° C. oven for 12 minutes. Then the assembly was removed from the oven, the specimen was demolded and placed in distilled water at 37° C. for 24 hours before testing. Specimens for example 15 were prepared by mixing one small scoop of catalyst and one large scoop of base (as per manufacturer's directions) for 30 seconds. The mold was packed and clamped as in Example 14 and placed in a 37° C. oven for 15 minutes. Then the assembly was removed, specimen was demolded, and placed in distilled water at 37° C. for 24 hours before testing. Six specimens of each material were prepared.

Testing was done using a crosshead speed of 10 mm/min. and a load of 5 Kg.

Tear strength was calculated as follows:

$$\text{Tear strength} = \frac{\text{kilograms of force at rupture} \times 9.807}{\text{cross-sectional area}} \times \frac{145 \text{ PSI}}{N/mm^2}$$

Elongation was determined at the rupture of the specimen.

Strain in tension was calculated by dividing the elongation by the gage length (22 mm) times 100.

Modulus of Elasticity was calculated using the automatic mode for which an overall slope is computed as a least-mean-square fit over all the data in the constant-slope region. The formula used was:

$$\text{Modulus of Elasticity} = \frac{\text{change in load}}{\text{change in elongation}} \times \frac{\text{gage length}}{\text{cross-sectional area}}$$

|  | Example 13 | Example 14 | Example 15 |
|---|---|---|---|
| Work Time | Unlimited | 5–8 Min. | 4–6 Min. |
| Set Time | Upon irradiation in 20–40 sec. | 8–10 Min. | 12 Min. |
| Depth of Cure (10 Sec) | 13–14 mm | — | — |
| Consistency | 24 mm | 20 mm | 20 mm |
| Strain in Compression | 2.0% | 1.16% | 0.28% |
| Tear Strength | 325.5 PSI | 118.9 PSI | 87.1 PSI |
| Elongation in Tensile | 9.2 mm | 0.4 mm | 0.10 mm |
| Strain in Tension | 40.2% | 1.8% | 0.45% |
| Modulus of Elasticity | 930 PSI | 0 Not Measurable | 0 Not Measurable |

While throughout this application the present invention of a treatment membrane has been described with respect to dental application, it will be obvious to those skilled to the art that there would be many general medical applications for which the invention would be well suited. It is therefore intended that the invention be understood to also include applicability in such uses.

While in accordance with the patent statutes, what is considered to be the preferred embodiment of the invention has been described, it will be obvious to those skilled in the art that numerous changes and modifications may be made therein without departing from the invention and it is therefore aimed in the apended claims to cover all such equivalent variations as fall within the true spirit and scope of the invention.

It is claimed:

1. A method of producing an elastomeric bandage in situ in the oral cavity of a mammal comprising:
    applying a fluid actinic light polymerizable composition comprising polymerizable organic compound and visible actinic light initiator to tissue in the oral cavity in need of the protection of a bandage,
    flowing said fluid polymerizable composition in direct contact with rigid dentition to provide a direct mechanical locking with said rigid dentition upon the setting of said fluid polymerizable composition, causing said fluid polymerizable composition to set by exposing said polymerizable composition to actinic light to form a elastomeric dental bandage mechanically locked to said rigid dentition.

2. The method of producing a dental bandage in the oral cavity of claim 1 wherein said polymerizable organic compound has a reaction functionality of two, said setting is at least in part in response to engagement of a surface of said fluid polymerizable composition by actinic light and said setting forms an elastomeric oral cavity dental bandage.

3. The method of producing a dental bandage in the oral cavity of claim 2 wherein said fluid actinic light polymerizable composition retains its fluid form for a period of at least two months as a one component composition when stored actinic light free, is applied from a syringe and is flowed to completely surround at least one tooth in direct contact with said tooth to provide said mechanical locking and is set completely surrounding said at least one tooth.

4. The method of producing a dental bandage in the oral cavity of claim 2 wherein said fluid actinic light polymerizable composition retains its fluid form for a period of at least two months as one component composition when stored actinic light free is applied from a syringe and is flowed to a wedged position in an embrasure between two teeth in direct contact with said teeth to provide said mechanical locking and is set in wedged position in said embrasure between said two teeth.

5. The method of producing a dental bandage in the oral cavity of claim 2 wherein said polymerizable organic compound is an oligomer that is a urethane acrylate and said actinic light initiator is activated by actinic light having a wave length of about 360–600 nm.

6. The method of producing a dental bandage in the oral cavity of claim 1 wherein said fluid actinic light polymerizable composition comprises therapeutic substance homogeneously mixed throughout, and after said setting said therapeutic substance is leachable in said oral cavity for a period of at least one week.

7. The method of producing a dental bandage in the oral cavity of claim 1, wherein said polymerizable organic compound comprises a compound of the general formula:

$R_1$ is

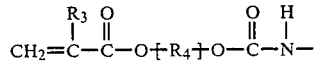

$R_2$ is $$CH_2=\overset{R_3}{\underset{|}{C}}-\overset{O}{\underset{\|}{C}}-O+R_4\overset{H}{\underset{|}{\rule{0pt}{1em}}}\overset{O}{\underset{\|}{N-C}}-O-$$

wherein
R$_3$ is H, F, CN or methyl
R$_3$ may be the same or different in each position
R$_4$ is a divalent hydrocarbon radical or benzene substituted divalent hydrocarbon radical having 2-100 carbon atoms and may be straight or branched chain or cyclic or a combination thereof, and is a polyurethane oligomer having a molecular weight of at least 600 said method comprising (a) cleaning and drying said rigid dental structure;
(b) thereafter flowing said fluid polymerizable composition directly against said rigid dental structure,
(c) curing said fluid dental polymerizable composition while it is directly engaged with said rigid dental structure to mechanically lock it therewith.

8. The method of producing a dental bandage in the oral cavity of claim 7 wherein said organic compound comprises a composition of the general formula:

$$CH_2=\overset{CH_3}{\underset{|}{C}}-\overset{O}{\underset{\|}{C}}-O-CH_2-CH_2-\overset{H}{\underset{|}{N}}-\overset{O}{\underset{\|}{C}}-O-(CH_2)_4-$$

$$-O-\overset{O}{\underset{\|}{C}}-\overset{H}{\underset{|}{N}}-CH_2-\overset{CH_3}{\underset{\underset{CH_3}{|}}{C}}-CH_2-\overset{}{\underset{\underset{CH_3}{|}}{CH}}-CH_2-CH_2-\overset{H}{\underset{|}{N}}-\overset{O}{\underset{\|}{C}}-O-$$

$$+R_7-O+_{\overline{x}}\overset{O}{\underset{\|}{C}}-\overset{H}{\underset{|}{N}}-CH_2-CH_2-\overset{}{\underset{\underset{CH_3}{|}}{CH}}-CH_2-\overset{CH_3}{\underset{\underset{CH_3}{|}}{C}}-CH_2-$$

$$-\underset{\underset{H}{|}}{N}-\underset{\underset{O}{\|}}{C}-O-CH_2-CH_2-O-\underset{\underset{O}{\|}}{C}-\underset{\underset{CH_3}{|}}{C}=CH_2$$

R$_7$ = Alkylene, and
x = 10 to 100 wherein.

9. The method of producing a dental bandage of claim 8 wherein said fluid actinic light curable composition includes said polymerizable organic compound in an amount of about 5 to 95% by weight of the total weight of said fluid actinic light curable composition; said actinic light initiator in an amount of about 0.001 to about 10% by weight of said polymerizable organic compound; and filler in an amount of about 5 to 95% by weight of the total weight of said fluid actinic light curable composition.

10. The method of producing a dental bandage in the oral cavity of claim 1 wherein said fluid actinic light polymerizable composition comprises therapeutic agent.

11. A method for producing an interoral drug delivery device in situ in a mammal comprising:
positioning a fluid polymerizable composition comprising polymerizable organic compound, polymerization initiator and therapeutic agent interorally by delivering said composition from a syringe into direct contact with rigid dentition,
modeling said fluid polymerizable composition to conform to the shape and position of said right dentition while it is interoral, and
polymerizing said fluid polymerizable composition in situ by the application of visible actinic light to produce an elastomeric drug delivery device which is mechanically interlocked with said rigid dentition.

12. The method of claim 11, wherein said fluid polymerizable composition comprises solid leachable material chosen from the group consisting of microcapsules, prepolymerized polymer microparticles including therapeutic agent and mixtures thereof having a particle size of less than about 250 microns chosen from the group consisting of water soluble and water disperable prepolymerized polymers and mixtures thereof.

13. The method of claim 11, wherein said polymerizable organic compound comprising comprises a compound of the general formula:

$$R_1+[A]R_2$$

R$_1$ is $$CH_2=\overset{R_3}{\underset{|}{C}}-\overset{O}{\underset{\|}{C}}-O+R_4+O-\overset{O}{\underset{\|}{C}}-\overset{H}{\underset{|}{N}}-$$

R$_2$ is $$CH_2=\overset{R_3}{\underset{|}{C}}-\overset{O}{\underset{\|}{C}}-O+R_4+\overset{H}{\underset{|}{N}}-\overset{O}{\underset{\|}{C}}-O-$$

wherein
R$_3$ is H, F, CN or methyl
R$_3$ may be the same or different in each position
R$_4$ is a divalent hydrocarbon radical or benzene substituted divalent hydrocarbon radical having 2-100 carbon atoms and may be straight or branched chain or cyclic or a combination thereof, and is a polyurethane oligomer having a molecular weight of at least 600;
wherein in said method said modeling includes forming said fluid polymerizable composition in sufficient juxtaposition to rigid dental structure to provide a mechanical locking with said rigid dental structure upon the polymerizing of said fluid polymerizable composition, and said polymerizing in situ bringing about a locking with said rigid dental structure,
and said method comprising cleaning and drying said rigid dental structure before positioning said fluid polymerizable composition.

14. A method of claim 13 wherein said fluid polymerizable includes said polymerizable organic compound in an amount of about 5 to 95% by weight of the total weight of said fluid actinic light curable composition; said actinic light initiator in an amount of about 0.001 to about 10% by weight of said polymerizable organic compound; and filler in an amount of about 5 to 95% by weight of the total weight of said fluid actinic light curable composition.

15. The method of claim 11 wherein said therapeutic substance is homogeneously mixed throughout said fluid polymerizable composition and after said setting is leachable in said oral cavity for a period of at least one week.

16. A method of producing a dental bandage in the oral cavity of a mammal comprising:
   acid etching the enamel of at least one tooth in the oral cavity
   applying a fluid visible actinic light polymerizable composition comprising a polymerizable organic compound and actinic light initiator to damaged tissue in the oral cavity,
   flowing said fluid polymerizable composition in sufficient juxtaposition to said at least one acid etched tooth to provide attachment of said polymerizable composition on setting thereof,
   setting said fluid polymerizable composition to attach to said at least one tooth and producing said oral cavity dental bandage.

17. The method of claim 16 in which said attachment of said polymerizable material to said at least one acid etched tooth is a mechanical locking thereof.

18. The method of claim 16 in which said attachment of said polymerizable material to said at least one acid etched tooth is an adhesive bonding thereto.

* * * * *